United States Patent [19]

Brunengraber et al.

[11] Patent Number: 5,126,373
[45] Date of Patent: Jun. 30, 1992

[54] COMPOSITION FOR PARENTERAL AND ORAL NUTRITION

[76] Inventors: Henri Brunengraber, 16700 S. Woodland Rd., Shaker Heights, Ohio 44120; Sylvain Desrochers, 5704 2e Avenue, Rosemont, Québec, Canada, H1Y 2Y6; Bernard R. Landau, 19501 S. Woodland Rd., Shaker Heights, Ohio 44122

[21] Appl. No.: 622,849

[22] Filed: Dec. 6, 1990

Related U.S. Application Data

[63] Continuation-in-part of Ser. No. 271,613, Nov. 15, 1988, Pat. No. 4,997,976.

Foreign Application Priority Data

Nov. 19, 1987 [CA] Canada .................. 555276

[51] Int. Cl.$^5$ ............................. A01N 37/02
[52] U.S. Cl. ...................... 514/547; 514/546
[58] Field of Search ................. 514/547, 546

[56] References Cited

FOREIGN PATENT DOCUMENTS 316993  5/1989  European Pat. Off. .
318357  5/1989  European Pat. Off. .
1172419 11/1969 United Kingdom .

Primary Examiner—Paul J. Killos
Attorney, Agent, or Firm—Reed Smith Shaw & McClay

[57] ABSTRACT

In accordance with the present invention, there is provided a composition for parenteral and oral nutrition, which comprises a compound of Formula I:

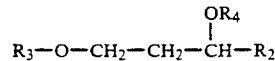

wherein
$R_2$ is methyl or ethyl;
$R_3$ and $R_4$ are independently

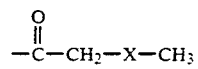

or H, and
X is —C=O or —HC—OH,
and mixtures thereof,
or pharmaceutically acceptable derivative, diastereoisomers or optical isomers thereof, in association with a pharmaceutically acceptable carrier, with the proviso that $R_3$ and $R_4$ cannot be H at the same time.

7 Claims, No Drawings

COMPOSITION FOR PARENTERAL AND ORAL NUTRITION

CROSS REFERENCE

This is a continuation-in-part of U.S. Ser. No. 271,613, filed Nov. 15, 1988, now U.S. Pat. No. 4,997,976

BACKGROUND OF THE INVENTION

In recent years, parenteral nutrition has been widely practiced although its use is often accompanied by undesirable side effects such as infection, thrombosis, catheter and air embolization, and metabolic problems.

The use of parenteral nutrition has proved to be an extremely important tool in the treatment of a wide variety of diseases. For example, mortality from acute alimentary failure as in enterocutaneous fistula, has been considerably reduced by parenteral nutrition. Patients who have had extensive intestinal resection for such condition as Crohn's disease and ulcerative colitis have maintained good health at home for a long time on parenteral nutrition.

Parenteral nutrition also reduces the risks accompanying surgery in under-nourished patients, and promotes tissue repair and immune response following major surgery, trauma, and especially burns or multiple fractures with sepsis. Furthermore, short term parenteral nutrition has been lifesaving in comatose patients and in intractable anorexia nervosa. Support with parenteral nutrition has permitted chemotherapy and radiation therapy in patients with cancer otherwise considered unsuitable for any treatment.

However, even though parenteral nutrition has proved to be useful and necessary over the years, the concentrated fat emulsions that are used for the preparation of suitable solutions are mainly responsible for the various side effects that are encountered. Hence, the ideal source of calories for parenteral nutrition should have a high caloric density, a total solubility in water, no ionic charge, thus avoiding the necessity of administering a counter ion like $Na^+$, good diffusibility through cell membranes to avoid hyperosmolality, rapid metabolism to acetyl-CoA and protein sparing action.

There are good reasons to believe that 1,3-butanediol, either as a DL mixture or as the D- or L-isomers can meet most of the above-mentioned criteria. The DL mixture has been investigated as a component of animal feed for a long time. When humans were fed a diet containing 5% of DL-1,3-butanediol, nitrogen was spared and there was no adverse effect. Furthermore, DL-1,3-butanediol alleviates the ethanol withdrawal syndrome in rats thus making it a potential therapeutic agent in human alcoholics. DL-1,3-butanediol is metabolised in the liver to DL-3-hydroxybutyrate via alcohol and aldehyde dehydrogenase; the D-β-hydroxybutyrate is in oxydo-reduction equilibrium with acetoacetate via the action of D-β-hydroxybutyrate dehydrogenase.

On the other hand, L-β-hydroxybutyrate is not a natural compound although it is very well used by mammalian cells. In addition, it has been demonstrated that L-1,3-butanediol is useful in reducing the blood glucose level of alloxan-diabetic rats.

However, although the use of butanediol in parenteral nutrition and diabetic control looks promising, the use of this substance presents some drawbacks. First, butanediol has a low molecular weight. As a result from this, high amounts of butanediol must be employed in order to provide sufficient calory intake. Furthermore, butanediol is a strong reducing agent and there is a possibility of creating an oxidation-reduction imbalance if parenteral nutrition is to be maintained for a long period of time.

Therefore, a parenteral composition comprising a compound replacing the usually employed concentrated fat emulsion and having a high molecular weight, a proper oxidation-reduction balance, as well as minimal side effects would be highly desirable.

SUMMARY OF THE INVENTION

In accordance with the present invention, there is provided a composition for parenteral and oral nutrition, which comprises a compound of Formula I:

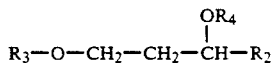

wherein
$R_2$ is methyl or ethyl;
$R_3$ and $R_4$ are independently

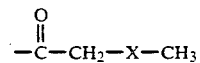

or H, and
X is $-C=O$ or $-HC-OH$,
and mixtures thereof,
or pharmaceutically acceptable derivative, diastereoisomers or optical isomers thereof, in association with a pharmaceutically acceptable carrier, with the proviso that $R_3$ and $R_4$ cannot be H at the same time.

In a second aspect of the present invention, there is provided a method for nutritional support of a patient, which comprises administering to said patient an effective amount of a compound of Formula I, or mixtures thereof.

DETAILED DESCRIPTION OF THE INVENTION

The present invention relates to a composition for parenteral or oral nutrition, which comprises a compound of Formula I:

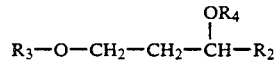

wherein
$R_2$ is methyl or ethyl;
$R_3$ and $R_4$ are independently

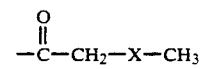

or H; and
X is $-C=O$ or $-HC-OH$;
and mixtures thereof,
or pharmaceutically acceptable derivative, diastereoisomers or optical isomers thereof, in association with a pharmaceutically acceptable carrier, with the proviso that $R_3$ and $R_4$ cannot be H at the same time.

These compounds are hereinafter generally referred to as butanediolacetoacetate when $R_2$ is methyl, and pentanediol-acetoacetate when $R_2$ is ethyl.

The terms butanediol-acetoacetate and pentanediol-acetoacetate is meant to include all the compounds and functional derivatives thereof represented by Formula I.

The compounds described herein contain chiral centers and may thus give rise to diastereoisomers and optical isomers. The composition of the present invention is meant to include all such possible diastereoisomers as well as their racemic and resolved optically active forms.

Generally speaking, when reference is made to the butanediolacetoacetate or pentanediol-acetoacetate compounds used in accordance with the present invention, it refers to their racemic mixtures containing both the D and L forms. However, there is an interest at producing the corresponding reduced 3-hydroxybutyrate derivatives, in particular DL-1,3-butanediol-DL-$\beta$-hydroxybutyrate, DL-1,3-pentanediol-DL-$\beta$-hydroxybutyrate, and corresponding D- and L- isomers. The L-isomers are particularly useful as an antidiabetic agent since their metabolism generates two molecules of L-$\beta$-hydroxybutyrate which, as mentioned earlier, has demonstrated interesting antidiabetic properties.

UTILITY

The compounds of Formula I are useful as total or partial replacement of the concentrated fat emulsions that are used for intravenous parenteral nutrition. These compounds may also be included in infant nutrition formulas preferably given orally to children suffering from various defects in $\beta$-oxidation of fatty acids, such as deficiencies in acyl-CoA dehydrogenase, hydroxymethyl-glutaryl-CoA lyase or carnitine, thereby alleviating some cases of the sudden infant death syndrome (SIDS) by which some newborns die of hypoglycemia related to impaired fatty acid oxidation.

Furthermore, during the suckling period and the following weeks, the brain of newborn mammals preferentially uses ketone bodies to synthesize large quantities of lipids which are used in the process of myelinization of neurons. Therefore, administration of a compound of Formula I, or mixtures thereof to children at risk for SIDS would not only spare the reserves of liver glycogen but also supply a fuel preferentially used by the developing brain.

The composition of the present invention allows treatment of patients suffering from fat malabsorption. Furthermore, under hypermetabolic conditions such as trauma, infection or large burns, ketone body concentrations in blood are very low. This is explained by the hypermetabolic state of the liver whose ATP requirements are greatly increased for the synthesis of shock proteins. Thus, fatty acid carbon is completely oxidized via the Krebs cycle, while little is spilled out as ketone bodies. Thus, in hypermetabolic states, the liver does not provide ketone bodies (a soluble form of fat) to peripheral tissues. Since ketone bodies are well used by peripheral tissues as a source of energy, they could be supplied in the form of butanediol-acetoacetate or pentanediol-acetoacetate to patients either orally or via a stomach tube.

The composition of the present invention also provides the replacement of glucose in peritoneal dialysis solutions. These solutions often contain high concentrations of glucose to prevent absorption of the solution's water and to remove the excess water from the patient. Unfortunately, this usually leads to undesirable hyperglycemia, especially in diabetic patients. Administration of compounds of Formula I either alone or in a composition, instead of glucose do not lead to hyperglycemia and supply an easily metabolisable fuel.

Also, the compound of Formula I could advantageously replace the ketogenic diet in the treatment of children suffering from either intractable epileptic seizures which cannot be controlled by medication or from inborn errors of metabolism, such as deficiency in pyruvate dehydrogenase accompanied or not by psychological and intellectual problems (certain forms of autism or Rett's disease).

When these children are treated with ketogenic high fat diet, there is poor compliance because of the unpalatability of the diet. In addition, any intake of carbohydrates can lead to either seizures or deterioration of the condition of the child since carbohydrates inhibit conversion of the fat in the ketogenic diet to ketone bodies. In contrast, the ketogenic potential of the compounds of Formula I is not affected by the presence of carbohydrate in the diet. Thus, it is likely that these children could be kept on a normal diet with addition of 5 to 10% of the daily caloric requirement as butanediol or pentanediol acetoacetate or $\beta$-hydroxybutyrate esters dissolved in fruit or vegetable juice or in chocolate drink.

Furthermore, when massively obese people are treated with total or almost total caloric restriction in a metabolic ward, it takes a few days for ketosis to develop in the patient. Once ketosis is developed, its appetite inhibiting effect helps the patient comply with the treatment. However, during the first few days of the treatment, when ketosis is still low, it is difficult and stressful for the patient to comply with the restrictions. It is hypothesized that ketosis could be rapidly induced during severe caloric restriction by giving the patient an appropriate amount of the butanediol or pentanediol esters of Formula I in divided doses over the first day. This would prime the ketotic state of the patient and allow him or her to adjust easily to the treatment.

It has also been noted that the administration of the mono- and diesters of acetoacetate of butanediol or pentanediol described herein have the following advantages over the administration of butanediol alone:

a) the metabolism of the esters in the liver after hydrolysis in plasma leads to mixtures of 3-hydroxybutyrate and acetoacetate which are in a physiological oxido-reduction ratio. In contrast, using butanediol alone leads to a mixture of 3-hydroxybutyrate and acetoacetate which is more reduced than physiological. Thus, the butanediol and pentanediol esters of acetoacetate could be included in general parenteral solutions as precursors of 3-hydroxybutyrate and acetoacetate and as oxido reduction buffers as recommended by R. L. Veech (Am. J. Clin. Nut., 44; 519–51, 1986).

b) the administration of esters of butanediol leads to a lower butanediol concentration in plasma thus alleviating any potential effect of this alcohol on the brain.

c) when butanediol or pentanediol derived from hydrolysis of its acetoacetate esters is oxidized in the liver to 3-hydroxybutyrate or 3-hydroxypentanoate, the bulk of the reducing equivalents (NADH)

generated by butanediol or pentanediol oxidation is trapped in acetoacetate and exported from the liver as 3-hydroxybutyrate or 3-hydroxypentanoate. Thus there is no oxido-reduction shift in the liver towards the more reduced state which could, under certain circumstances, inhibit gluconeogenesis (synthesis of new glucose molecules) and lead to hypoglycemia.

Finally, butanediol-acetoacetate and butanediol-bis-acetoacetate and corresponding pentanediol derivatives can be used as a component of animal feed since ketone bodies are preferentially used by lactating mammary glands and the developing brain. For example, it could be used as a food supplement in the mash of sows during the last third of pregnancy and in the lactating period. It can also be used for bottle-feeding of new born pigs too weak to compete for their mother's nipple and it can be used in the mash of newborn chicken.

CONCENTRATION IN PARENTERAL SOLUTIONS

The concentration of the compound of Formula I in the composition of the present invention for parenteral administration will depend on various factors but will generally range between 5 and 100% wt/vol. This concentration may be that which is intended for use, e.g. about from 5 to 20% wt/vol, or may be more concentrated, e.g. about from 25 to 100% wt/vol. or the limit saturated concentration of the compound.

As for the butanediol-bis-acetoacetate, its concentration in parenteral solutions will generally range between 5 and 100% wt/vol. Again, the concentration may be that which is intended for use, e.g. about from 5 to 15% wt/vol., or may be more concentrated, e.g. 10 to 100% wt/vol. in the case of saturated solutions. When it is intended to use a mixture of butanediol-acetoacetate and butanediol-bis-acetoacetate, the proportions of each compound will generally range between 1:4 and 4:1% wt/vol., with concentration values ranging from 5 to 20% wt/vol. for ready to use solutions and from 5 to 100% wt/vol. for concentrated stock solutions. The same proportions apply for the corresponding pentanediol acetoacetate and pentanediol-bis-acetoacetate.

Concentrated solutions are maintained at a greater concentration to enhance the compound's stability during autoclaving or storage. Such solutions are then diluted to the desired administration concentration at some convenient point before use. If necessary, the compounds of Formula I or mixtures thereof need not be incorporated in an aqueous solution at all until reconstitution before administration. This, however, is not as commercially desirable as supplying a ready-to-use solution.

The solutions of butanediol-acetoacetate, butanediol-bis-acetoacetate, pentanediol-acetoacetate or pentanediol-bis-acetoacetate, or mixtures thereof frequently will be mixed with other nutrients or with drugs. Such other nutrients may include nitrogen sources such as aminoacids, vitamins, minerals, and electrolytes including trace elements. Other calory sources such as carbohydrates or lipids may not be needed but may also be maintained in the solution. The aminoacids are mixed with one or more compounds of Formula I, prior to or after sterilization. A mixture of essential aminoacids nutritionally balanced will ordinarily be sufficient, although no essential aminoacids may be included. The proportions may be adjusted for special disease states, e.g., inborn errors of metabolism, in accord with known practice.

PACKAGING OF PARENTERAL SOLUTIONS

The solutions containing the composition of the present invention are packaged in conventional parenteral solution containers, either glass or thermoplastic flexible bags. Such containers are sterile, sealed and will contain means for communicating with the patient's circulation, either alone or in concert with other devices. Typically, the means for communicating with the patient's circulation will be a fragile member associated with a container which is adapted to enter into fluid communications with an administration set. Such sets are well known in the art.

ADMINISTRATION AND DOSAGE

The solutions containing the composition of the present invention usually are parenterally administered by infusion into a peripheral vein although they may also be infused through a central veinous catheter. The solutions are infused at a rate sufficient to maintain the nutritional status of the patient in concert with the intake of other nutrients. Infusion will be ordinarily about from 1 to 7 Kcal/kg patient weight/day for an adult patient and from 1 to 30 Kcal/kg patient weight/day for a pediatric patient but the amount administered parenterally will depend upon the patient's metabolic needs.

The compounds of Formula I or mixtures thereof can be taken orally, and they have the advantage of a higher energy content than glucose so are less likely to cause diarrhea or other intestinal distress at a given Kcal dose when compared to glucose. The compounds of Formula I, either administered alone or in combination with other nutrients as described above or with drugs, can be taken by gastric tube or as a component of ordinary meals. Since these compounds are to function as nutrients, they are supplied in quantities sufficiently high to provide greater than 15% preferably greater than 25% of the calories required by the patient.

PREPARATION OF BUTANEDIOL-ACETOACETATE AND BUTANEDIOL-BIS-ACETOACETATE

The butanediol or pentanediol acetoacetate compounds of Formula I are generally prepared by reacting, in the presence of a catalyst, equimolar amounts of diketene and a suitable diol. Preferably, the catalyst is anhydrous sodium acetate, but any suitable acid catalyst can be used, while the diol is selected from 1,3-butanediol or 1,3-pentanediol. The temperature at which the reaction is to be performed may vary from 25° to 120° C. Following the complete addition of the diketene, the solution is then purified by column chromatography on silicon dioxide with a mixture of ethyl acetate, methylene chloride as preferred solvents for chromatography purification.

Alternatively, purification can be conducted through filtration on flash silica and elution with a mixture of hexane-ethylacetate. Also it is possible to purify the compounds of Formula I through dissolution in water and treatment with a mixture of anion- and cation-exchange resins. The discolorized and neutral solution is then extracted with chloroform. The extract is dried on sodium sulfate, filtered and evaporated under vacuum.

The butanediol-bis-acetoacetates are known compounds and their preparation is described in Beilsteins Baud III, II 3,659. These compounds and corresponding pentanediol-bis-acetoacetates are prepared in the same manner as described above, except that two equivalents of diketene are reacted with the diol, instead of 1 equivalent.

The present invention is further defined by reference to the following examples which are intended to be illustrative and not limiting.

EXAMPLE 1

Process for the preparation of 1,3-butanediol-acetoacetate 5 mmol of triethylamine are mixed with 1 mole of 1,3-butanediol. The mixture is stirred on an ice bath and 1 mole of diketene is added dropwise over 1.5 hours. Stirring is continued for 5 to 7 hours at 0° C., then for a further 15 hours at room temperature. The reaction is monitored occasionally by proton NMR. This procedure yields a mixture of butanediol-acetoacetate and butanediol-diacetoacetate in proportion 77:23 (assayed by gas chromatography). Butanediol-bis-acetoacetate can be obtained as a main product by reacting 1 mole of butanediol with 2 moles of diketene.

A mixture of acetoacetic acid, 3-hydroxybutyl ester (A) and acetoacetic acid, 1-methyl 3-hydroxypropyl ester (B) is obtained.

| MOLECULAR WEIGHT | 174.20 |
|---|---|
| REFRACTIVE INDEX | $1.4462^{25}$ |
| BOILING POINT (°C.) | $100^{.05 \, mm}$ |
| COMPOUND A/COMPOUND B | 3.043 |

Purification of product of synthesis can be conducted by either:
  a) filtration on flash silica and elution with a mixture of hexane-ethylacetate 60:40 yields a mixture of mono-and diester. (Yield 84%) On this column, the order of elution is: the diester, the monoester, and trace of unreacted butanediol;
  b) dissolution in water and treatment with a mixture of anion-and cation-exchange resins. The discolorized and neutral solution is extracted with chloroform. The extract is dried on anhydrous sodium sulfate, filtered, and evaporated under vacuum. Yield of synthesis is 85%.

The following NMR and infrared spectra were obtained:

| PROTON NMR SPECTRUM ASSIGNMENTS (ppm) ||
|---|---|
| A 1.23,d,3H,$CH_3$ | G 3.67,t,2H,$CH_2$ |
| B 1.30,d,3H,$CH_3$ | H 4.26,t,2H,$CH_2$ |
| C 1.80,m,4H,$CH_2$ | I 4.28,m,1H,CH |
| D 1.96,s,6H,$CH_3$ | J 4.96,s,1H,CH |
| E 2.27,s,6H,$CH_3$ | K 6.17,m,1H,CH |
| F 3.47,s,4H,$CH_2$ | SOLVENT: $CDCl_3$ |
|  | REFERENCE TMS |
| CARBON-13 NRM SPECTRUM ASSIGNMENTS (ppm) ||
| A 20.1  B 21.1 | C 23.5 |
| D 30.1  E 37.7 | F 38.0 |
| G 38.7  H 49.9 | I 50.3 |
| J 58.5  K 61.2 | L 62.7 |
| M 64.5  N 69.7 | O $CDCl_3$ |
| P 89.6  Q 90.3 | R 167.1 |
| S 167.3  T 200.9 | U UNOBSERVED |
|  | SOLVENT $CDCl_3$ |
|  | REFERENCE TMS |

EXAMPLE 2

Using the processes described in Example 1, corresponding 1,3-pentanediol derivatives are prepared. Esters were analyzed by GC-MS as their bis-tert-butyldimethylsilyl (TBDMS) ether. Analysis of the TBDMS derivatives of esters was performed on an HP 5988A GC-MS (Hewlett-Packard Canada, Pointe-Claire, Québec). Mass spectrometer conditions in positive chemical ionization mode included: ion source temperature, 200°; transfer line temperature, 265°; emission current, 300 μA; ammonia pressure, 1 to $2 \times 10^{-4}$ torr and electron energy, 100–250 eV. Briefly, N-methyl-N-(t-butyldimethylsilyl)-trifluoroacetamide (0.50 ml) is added to about 2 μg of the purified esters. After 20 min incubation at 60° C., 1 μl is injected into the gas chromatograph.

The CI mass spectra of purified monoesters pentanediol-acetoacetate and diester pentanediol-bis-acetoacetate showed a peak at m/z 417 and m/z 501, respectively. These peaks correspond to the $[M+H]^+$ ion of esters of 1,3-pentanediol.

EXAMPLE 3

All the following experiments have been conducted on unanesthetized animals.

Young pigs, weighing 20 to 25 kg, were fitted with permanent catheters in a jugular vein, carotid artery and in the stomach (gastrostomy catheter). After one week recovery, the animals were subjected to one of the following protocols. The pigs were given equicaloric amount of either:
  (i) RS-butanediol alone,
  (ii) a mixture of mono and diester of butanediol-acetoacetate, in proportion of about 70:30;
  (iii) a mixture of mono and diester of butanediol-acetoacetate, in proportion of about 30:70.

Some animals received the substances by constant intravenous infusion for 3 h at a rate corresponding to 25% of the hourly caloric requirement of pigs that wt. Other animals received an intragastric bolus at a dose corresponding to 15% of the daily caloric requirements (considering that pigs eat two meals a day, and that each meal should contain 15% of the calories as RS-butanediol or its acetoacetate esters).

Glucose levels

In all groups, glucose levels remained at pre-infusion or pre-bolus levels. Thus, at the dose administered, RS-butanediol and its esters do not exert a hypoglycemic effect, as would be the case with ethanol.

RS-butanediol concentration

When the compounds were administered intravenously, RS-butanediol concentrations reached 0.6 mM in animals receiving RS-butanediol. However, when butanediol was administered intravenously in the form of its esters, the concentration of free butanediol never exceeded 0.15 mM.

When RS-butanediol was given as an intragastric bolus, the concentration of butanediol in the blood reached 25 mM, and then decreased linearly over 4 h. When the esters were administered as an intragastric bolus, the concentration of butanediol in blood peaked at about 2 mM and decreased linearly over 4 h. Thus, it appears that even with a large intragastric bolus, the concentration of alcoholic equivalents is rather low when the butanediol esters are given. For comparison, note that when ethanol is administered, the legal limit for driving an automobile is 17 mM.

Ketone body concentrations

The total concentration of physiological and unphysiological ketone bodies (R-3-hydroxybutyrate+S-3-hydroxybutyrate+acetoacetate) never exceeded 0.8 mM in the animal receiving RS-butanediol by the continuous intravenous route. When the esters were given intravenously, the concentration of total ketone bodies never went above 0.5 mM. In animals given the compounds as intragastric boluses, total ketone body concentration was about 1.5 mM in animals given RS-butanediol, and peaked at 3–4 mM in animals given the esters. Therefore, there was no marked acidosis in any of the groups.

Redox parameters

The ratio [lactate]/[pyruvate] in the blood of all the pigs remained at the physiological level of 12, throughout the experiments with esters. Therefore, there was no redox shift as is known to occur with ethanol. Note that with ethanol, it is this redox shift, i.e. an increase in [NADH]/[NAD+], which is responsible for inhibition of gluconeogenesis and thus alcoholic hypoglycemia. The problem does not seem to arise with the butanediol esters, under the present conditions.

The [R-3-hydroxybutyrate]/[acetoacetate] ration (which reflects the mitochondrial [NADH]/[NAD+]) was increased in experiments with RS-butanediol but was clamped at physiological levels (0.6–0.8) in animals given the esters. The clamping of the ratio can be explained as follows. RS-butanediol, derived from hydrolysis of the esters, is oxidized in the liver to RS-3-hydroxybutyrate+2 NADH. These NADH are trapped by the acetoacetate released from the esters. Therefore, the butanediol-acetoacetate esters do not perturb the oxido-reduction status of the liver. In addition, the reducing equivalents, generated by RS-butanediol oxidation in the liver, are exported to peripheral tissues, in the form of R-3-hydroxybutyrate. Thus, neither carbon, nor hydrogen from the butanediol esters remains in the liver.

Concentrations of non-hydrolyzed esters

The concentration of non-hydrolyzed mono- and diesters reached a plateau at about 40 μM in animals given the esters by continuous intravenous infusion. After the end of the infusion, the concentration of esters in blood decreased to undetectable levels (<5 μM) within 10 min. In animals receiving the esters by intragastric bolus, the concentration on non-hydrolyzed esters in the blood was undetectable throughout the experiment.

The esterase activity for the butanediol esters is about 1 U/ml plasma and 15 U/g liver. The absence of detactable butanediol esters in blood after administration of intragastric bolus stems probably from the action of gastrointestinal and heptic esterases.

In other experiments, the volume of distribution of butanediol is equal to 2/3 of the body wt, i.e. total body water. Also, butanediol distributes into total body water at the same rate as a tracer of water. Therefore, butanediol liberated in blood from plasma esterases does not exert any osmotic effect.

The above experiments show that at the dose administered, the esters of 1,3-butanediol and acetoacetate lead to minimal ketosis, which should not affect acid/base status. In addition, administration of the esters leads to very low concentrations of butanediol in the blood which should not have harmful effects. The very low level of unhydrolyzed esters in the plasma during intravenous infusion shows that plasma esterases hydrolyze the esters very rapidly to RS-butanediol and acetoacetate. Lastly, administration of the esters does not induce hypoglycemia.

Since 1,3-pentanediol has evident chemical structure similarity with 1,3-butanediol, preliminary results have shown that 1,3-pentanediol monoesters or diesters possess the same properties as the corresponding butanediol derivatives. RS-1,3-pentanediol (PD) is a gluconeogenic and a ketogenic substrate, and therefore is oxidized in liver by alcohol and aldehyde dehydrogenase to RS-3-hydroxypentanoate (RS-BHP). R-BHP should equilibrate with 3-ketopentanoate (BKP, an analog of acetoacetate) via mitochondrial R-BHB dehydrogenase. BKP is probably activated in peripheral tissues to BKP-CoA which, via thiolase, would yield propionyl-CoA+acetyl-CoA. S-BHP is probably activated in mitochondria of liver (and possibly of peripheral tissues) to S-BHP-CoA, an intermediate in the β-oxidation of odd-chain fatty acids. S-BHP-CoA via S-3-OH-acyl-CoA dehydrogenase and thiolase yields propionyl-CoA+acetyl-CoA. In liver and kidney, propionyl-CoA is gluconeogenic. In other organs, such as the heart, propionyl-CoA is converted to methylmalonyl-CoA, then to succinate which enters the citric acid cycle.

What is claimed is:

1. A composition for nutritional support, which comprises a compound of Formula I:

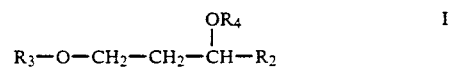

wherein
R$^2$ is methyl or ethyl;
R$_3$ and R$_4$ are independently

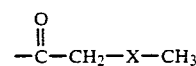

or H; and
X is —CH—OH or —C=O;
or mixtures thereof,
or pharmaceutically acceptable derivative, diastereoisomers or optical isomers thereof, in association with a pharmaceutically acceptable carrier, with the proviso that R$_3$ and R$_4$ cannot be H at the same time.

2. A composition according to claim 1, wherein said compound is present in an amount varying from about 5 to about 100% wt/vol.

3. A composition according to claim 1, further comprising nutrients or drugs.

4. A method for nutritional support of a patient which comprises administering to said patient an effective amount of a compound of Formula I:

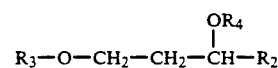

wherein
R$^2$ is methyl or ethyl;
R$_3$ and R$_4$ are independently

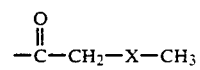

or H; and

X is —CH—OH or —C=O;

or mixtures thereof, or pharmaceutically acceptable derivative, diastereoisomers or optical isomers thereof, in association with a pharmaceutically acceptable carrier, with the proviso that $R_3$ and $R_4$ cannot be H at the same time.

5. A method according to claim 4, wherein said compound is administered in admixture with a pharmaceutically acceptable carrier.

6. A method according to claim 4, wherein said compound is administered in admixture with nutrients or drugs.

7. A method according to claim 5, wherein the amount of compound of Formula I is from about 5 to about 100% wt/vol.

* * * * *